(12) United States Patent
Preda et al.

(10) Patent No.: US 8,962,888 B2
(45) Date of Patent: Feb. 24, 2015

(54) FORMING SPHERICAL CRYSTAL HABIT

(71) Applicant: Physical Sciences, Inc., Andover, MA (US)

(72) Inventors: Dorin V. Preda, Medford, MA (US); Prakash B. Joshi, Andover, MA (US); Anait (Tsinberg) Scherer, Somerville, MA (US); Laurel A. Vernarelli, Somerville, MA (US)

(73) Assignee: Physical Sciences, Inc., Andover, MA (US)

( * ) Notice: Subject to any disclaimer, the term of this patent is extended or adjusted under 35 U.S.C. 154(b) by 16 days.

(21) Appl. No.: 13/786,715

(22) Filed: Mar. 6, 2013

(65) Prior Publication Data
US 2014/0155654 A1 Jun. 5, 2014

Related U.S. Application Data

(60) Provisional application No. 61/732,649, filed on Dec. 3, 2012.

(51) Int. Cl.
C07C 277/00 (2006.01)
C07C 279/00 (2006.01)
C07C 279/02 (2006.01)

(52) U.S. Cl.
CPC .................................... C07C 279/02 (2013.01)
USPC ......................................................... 564/241

(58) Field of Classification Search
CPC .. C07C 277/08; C07C 277/06; C07C 279/08; C07C 279/12
See application file for complete search history.

(56) References Cited

U.S. PATENT DOCUMENTS

2008/0292642 A1* 11/2008 Borhani et al. ............ 424/172.1

FOREIGN PATENT DOCUMENTS

WO WO 2010092355 * 8/2010

OTHER PUBLICATIONS

Spear, RJ et al., "Conversion of Propellant Grade Picrite to Spherical Nitroguanidine, an Insensitive Filler for Melt-Cast TNT Formulations," Materials Research Laboratory (1991), 43 pages.
Powala, D. et al., "Spherical Nitroguanidine as Component of High Explosives," NTREM Meeting, Institute of Industrial Organic Chemistry, Military University of Technology, Czech Republic (2004), pp. 606-613.
McKenney Jr., R.L. et al., "Small-Scale Testing of High Bulk Cubical and Spherical Nitroguanidine for Comparative Evaluation," Final Report, Wright Laboratory, Armament Directorate, Air Force Material Command, Florida (Aug. 1993), 20 pages.

* cited by examiner

Primary Examiner — Rosalynd Keys
Assistant Examiner — Jennifer C Sawyer
(74) Attorney, Agent, or Firm — Proskauer Rose LLP

(57) ABSTRACT

Methods for forming spherical crystal habit are shown. A needle-shaped crystal habit, a solvent, and a surfactant are combined and dissolved forming a first solution. The first solution and an anti-solvent are combined forming a second solution. The second solution is cooled. Spherical crystal habit is formed.

24 Claims, 8 Drawing Sheets

FORMING SPHERICAL CRYSTAL HABIT

CROSS REFERENCE TO RELATED APPLICATIONS

This application claims priority to U.S. Provisional Patent Application No. 61/732,649, filed Dec. 3, 2012.

GOVERNMENT RIGHTS

The invention was made with government support under the U.S. Army Research Laboratory contract number W911QX-08-C-0015. The government may have certain rights in the invention.

FIELD OF THE INVENTION

The invention relates generally to methods for forming spherical crystal habit from starting materials (e.g., needle-shaped crystal habit).

BACKGROUND

Insensitive munitions can be characterized as munitions that can withstand mechanical shock, fire, and impact, while retaining the ability to explode upon ignition. Nitroguanidine (NQ), a colorless crystalline solid, can be used as a material in insensitive munitions. One readily available form of NQ is NQ in the form of needle-shaped crystal habit. In this form, NQ can have a high surface area and low density. The high surface area of the NQ can increase viscosity of the NQ. The high surface area of the NQ can result in low fluidity of the NQ and/or difficulty when manufacturing munitions. The low density of the NQ can contribute to manufacturing difficulty, as high bulk density material can be easier to pack tightly when manufacturing munitions.

Some current methods attempt to overcome these difficulties by recrystallizing NQ into high bulk density cubic crystals. However, high bulk density cubic NQ can also have a high surface area and/or sensitivity to environmental stimuli and thermal conditions. In forming the high bulk density cubic NA, control of particle size and/or morphology can be difficult.

Therefore, it is desirable to recrystalize NQ into a form exhibiting low surface area. It is also desirable to recrystalize NQ into a form having high bulk density. It is also desirable to recrystalize NQ into a form that is less sensitive to environmental stimuli and thermal conditions. It is also desirable recrystalize NQ such that particle size and morphology can be more easily controlled. It is also desirable to use a form of NQ starting material that can be handled in the laboratory setting.

SUMMARY OF THE INVENTION

In one aspect, the invention involves a method of forming a spherical crystal habit. The method also involves forming a first solution by combining a needle-shaped crystal habit, a solvent, and a surfactant. The method also involves dissolving the needle-shaped crystal habit by heating the first solution to a desired temperature. The method also involves forming a second solution by combining the first solution with an anti-solvent. The method also involves cooling the second solution.

In some embodiments, the needle-shaped crystal habit is nitroguanidine. In some embodiments, the needle-shaped crystal habit that is combined to form the first solution is 3 grams of nitroguanidine. In some embodiments, the solvent includes N-methylpyrrolidone. In some embodiments, the solvent that is combined to form the first solution is 9 to 12 milliliters of N-methylpyrrolidone. In some embodiments, the surfactant includes Polysorbate 20. In some embodiments, the surfactant that is combined to form the first solution is 50 to 150 microliters of Polysorbate 20.

In some embodiments, combining the needle-shaped crystal habit, the solvent, and the surfactant further involves agitating the first solution. In some embodiments, agitating the first solution further involves shaking, stirring, manual combining, mechanical combining, or any combination thereof. In some embodiments, combining the needle-shaped crystal habit, the solvent, and the surfactant further involves stirring with a magnet.

In some embodiments, heating the first solution further involves uniformly distributing heat to the first solution. In some embodiments, the desired temperature is at least 80° C. In some embodiments, dissolving the needle-shaped crystal habit further involves shaking, stirring, manual combining, mechanical combining, or any combination thereof. In some embodiments, dissolving the needle-shaped crystal habit further involves stirring the first solution with a magnet.

In some embodiments, the anti-solvent includes acetone. In some embodiments, the anti-solvent is 120 to 200 milliliters of acetone. In some embodiments, forming the second solution further involves cooling the anti-solvent prior to combining the first solution with the anti-solvent. In some embodiments, cooling the anti-solvent further involves freezing, refrigerating, maintaining at room temperature, or any combination thereof In some embodiments, forming the second solution further involves combining an amount of anti-solvent greater than an amount of solvent. In some embodiments, forming the second solution further involves shaking, stirring, manual combining, mechanical combining or any combination thereof In some embodiments, forming the second solution further involves stirring with a magnet.

In some embodiments, cooling the second solution further involves freezing, refrigerating, maintaining at room temperature, or any combination thereof.

In another aspect, the invention involves a method of forming a spherical crystal habit. The method also involves forming a first solution by combining a needle-shaped crystal habit, a solvent, and a surfactant. The method also involves agitating the first solution by shaking, stirring, manually combining, mechanically combining, or any combination thereof The method also involves dissolving the needle-shaped crystal habit by uniformly distributing heat to the first solution at a desired temperature of at least 80° C. The method also involves cooling an anti-solvent by freezing, refrigerating, maintaining at room temperature, or any combination thereof The method also involves forming a second solution by combining the first solution with the anti-solvent. The method also involves agitating the second solution by shaking, stirring, manually combining, mechanically combining, or any combination thereof The method also involves cooling the second solution by freezing, refrigerating, maintaining at room temperature, or any combination thereof.

In yet another aspect, the invention includes a spherical crystal habit nitroguanidine. The process of forming the spherical crystal habit nitroguanidine involves forming a first solution by combining a needle-shaped crystal habit, a solvent, and a surfactant. The process of forming the spherical crystal habit nitroguanidine also involves dissolving the needle-shaped crystal habit by heating the first solution to a desired temperature. The process of forming the spherical crystal habit nitroguanidine also involves forming a second solution by combining the first solution with an anti-solvent.

The process of forming the spherical crystal habit nitroguanidine also involves cooling the second solution.

Advantages of the invention include recrystalizing NQ into a form exhibiting low surface area. Advantages of the invention also include recrystalizing NQ into a form having high bulk density. Advantages of the invention also include recrystalizing NQ into a form that is less sensitive to environmental stimuli and thermal conditions. Advantages of the invention also include recrystalizing NQ such that particle size and morphology can be more easily controlled. Advantages of the invention also include using a form of NQ starting material that can be handled in the laboratory setting.

Other aspects and advantages of the invention will become apparent from the following detailed description, taken in conjunction with the accompanying drawings, illustrating the principles of the invention by way of example only.

BRIEF DESCRIPTION OF THE DRAWINGS

The foregoing and other objects, features, and advantages of the present invention, as well as the invention itself, will be more fully understood from the following description of various embodiments, when read together with the accompanying drawings.

DETAILED DESCRIPTION

Generally, the invention involves a method for forming a spherical crystal habit. A first solution is formed by combining a needle-shaped crystal habit, a solvent, and a surfactant. The needle-shaped crystal habit is dissolved by heating the first solution to a desired temperature. An anti-solvent is combined with the first solution to form a second solution. The second solution is cooled.

In some embodiments, a needle-shaped crystal habit nitroguanidine (NQ) is combined with a solvent and a surfactant to form a first solution. Once the materials are combined, the first solution is heated to a desired temperature to dissolve the needle-shaped crystal habit NQ. Upon dissolving the needle-shaped crystal habit NQ, a second solution is formed by combining the first solution with an anti-solvent. Cooling the second solution allows the spherical crystal habit NQ to form.

Figure 1:
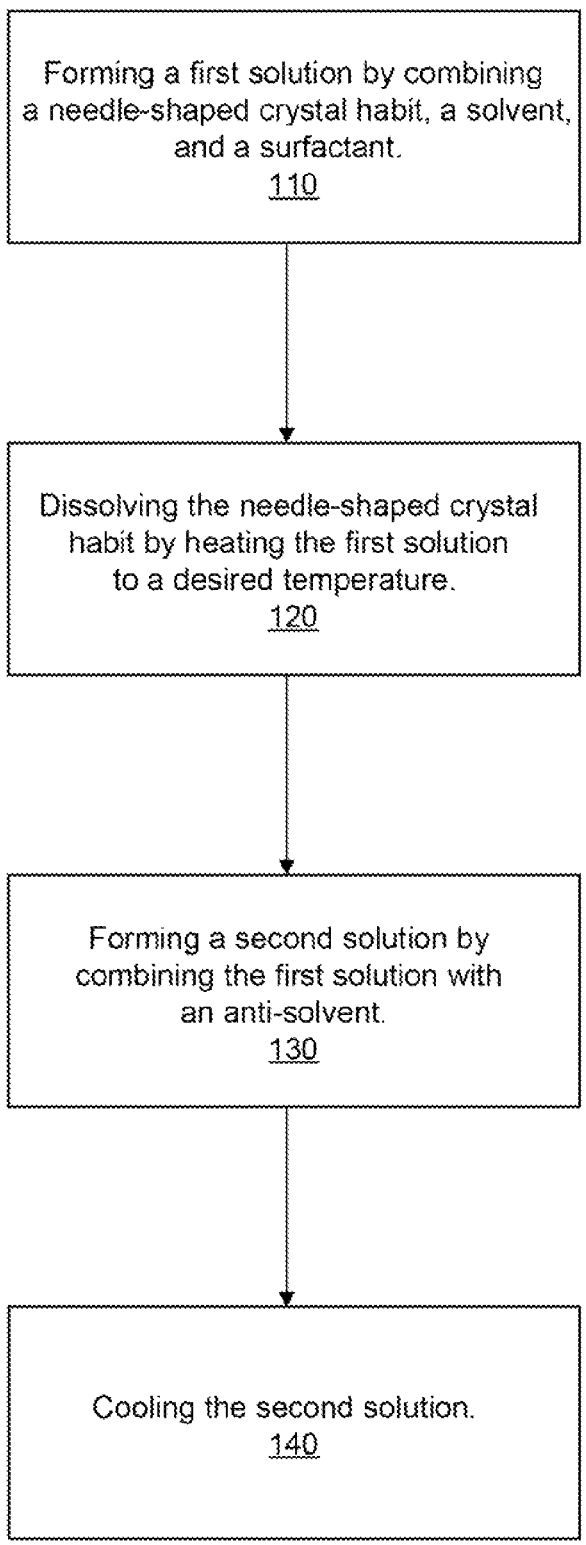
FIG. 1 is a flow chart showing a method of forming a spherical crystal habit, according to an illustrative embodiment of the invention.

FIG. 1 is a flow chart showing a method 100 of forming a spherical crystal habit, according to an illustrative embodiment of the invention.

Figure 2:
FIG. 2 is an image of nitroguanidine (NQ) in needle-shaped form, according to an illustrative embodiment of the invention.

The method involves forming a first solution by combing a needle-shaped crystal habit, a solvent, and a surfactant (Step 110). In some embodiments, the needle-shaped crystal habit is NQ. In some embodiments, the needle-shaped crystal habit is 3 grams of NQ. FIG. 2 is an image of NQ in needle-shaped form, according to an illustrative embodiment of the invention.

Turning back to FIG. 1, in some embodiments, the solvent includes N-methylpyrrolidone. In various embodiments, the solvent is 9 to 12 milliliters of N-methylpyrrolidone. In some embodiments, the surfactant includes Polysorbate 20. In some embodiments, the surfactant is 50 to 150 microliters of Polysorbate 20.

In various embodiments, the needle-shaped crystal habit, the solvent, and the surfactant are combined in a glass vial and/or an Erlenmeyer flask. It is apparent to one of ordinary skill in the art that any container suitable for combining can be used.

In some embodiments, the needle-shaped crystal habit, the solvent, and the surfactant are combined by agitating the first solution. In various embodiments, agitating the first solution involves shaking and/or stirring the first solution. In various embodiments, the combining the first solution is manual (e.g., performed by a human) and/or mechanical (e.g., performed by a machine). In some embodiments, the needle-shaped crystal habit, the solvent, and the surfactant are combined by stirring with a magnetic bar.

The method also involves dissolving the needle-shaped crystal habit by heating the first solution to a desired temperature (Step 120).

Figure 3:
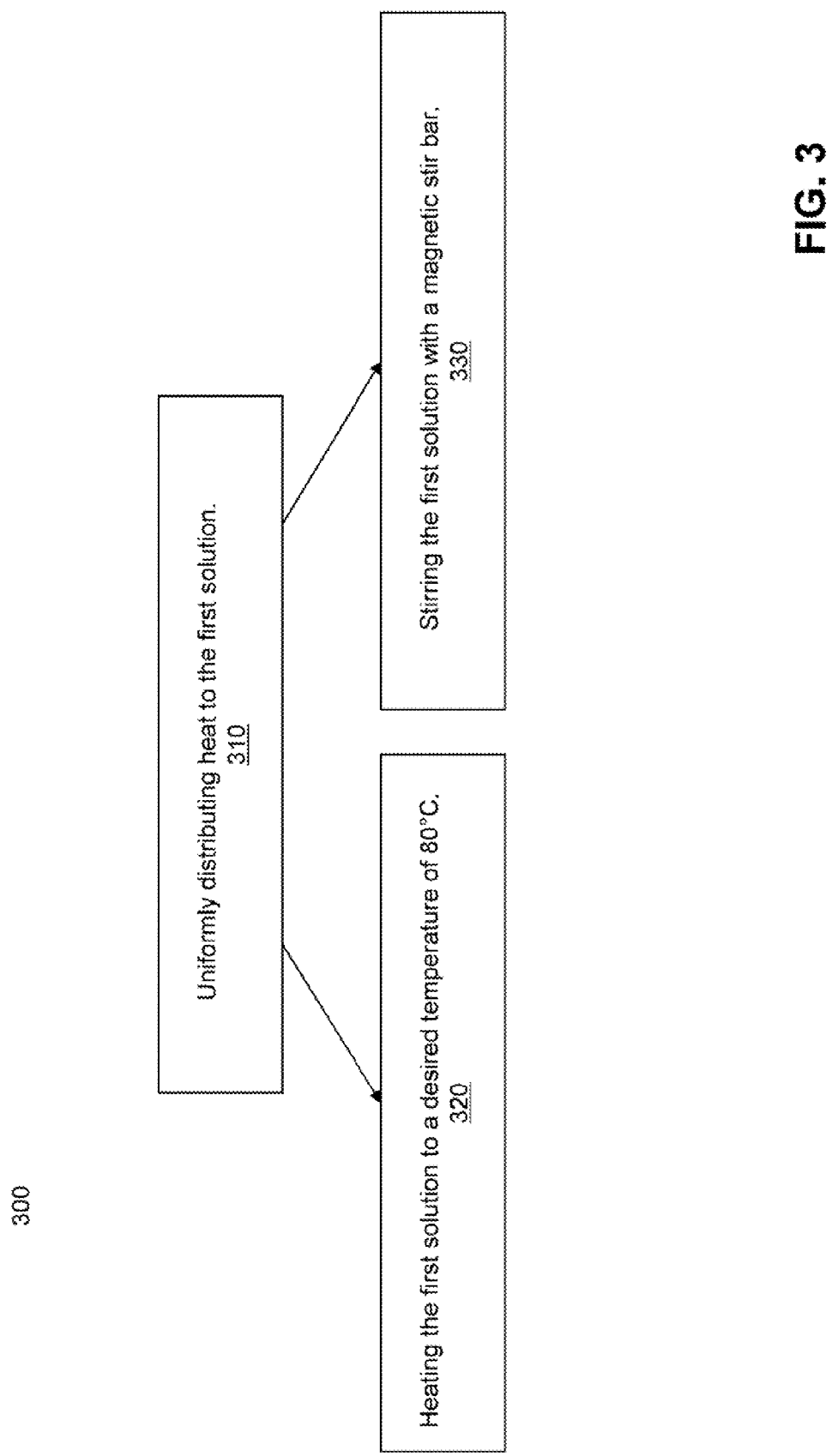
FIG. 3 is a flow chart showing a method of dissolving the needle-shaped crystal habit, according to illustrative embodiments of the invention.

FIG. 3 is a flow chart showing a method 300 of dissolving the needle-shaped crystal habit, according to illustrative embodiments of the invention.

The method involves uniformly distributing heat to the first solution (e.g., using a hot plate equipped with an insert fitted to the vial) (Step 310). The method also involves heating the first solution to a desired temperature (Step 320). In some embodiments, the desired temperature is the temperature that fully dissolves the needle-shaped crystal habit. In some embodiments, the desired temperature is 80° C. The method also involves stirring the first solution during heating with a magnetic bar (Step 330). In various embodiments, stirring the first solution during heating is manual (e.g., performed by a human) and/or mechanical (e.g., performed by a machine). In some embodiments, the first solution is stirred with a magnetic bar after heating.

Turning back to FIG. 1, the method also involves forming a second solution by combining the first solution with an anti-solvent (Step 130). In some embodiments, the anti-solvent includes acetone. In some embodiments, the anti-solvent is 120 to 200 milliliters of acetone.

Figure 4:
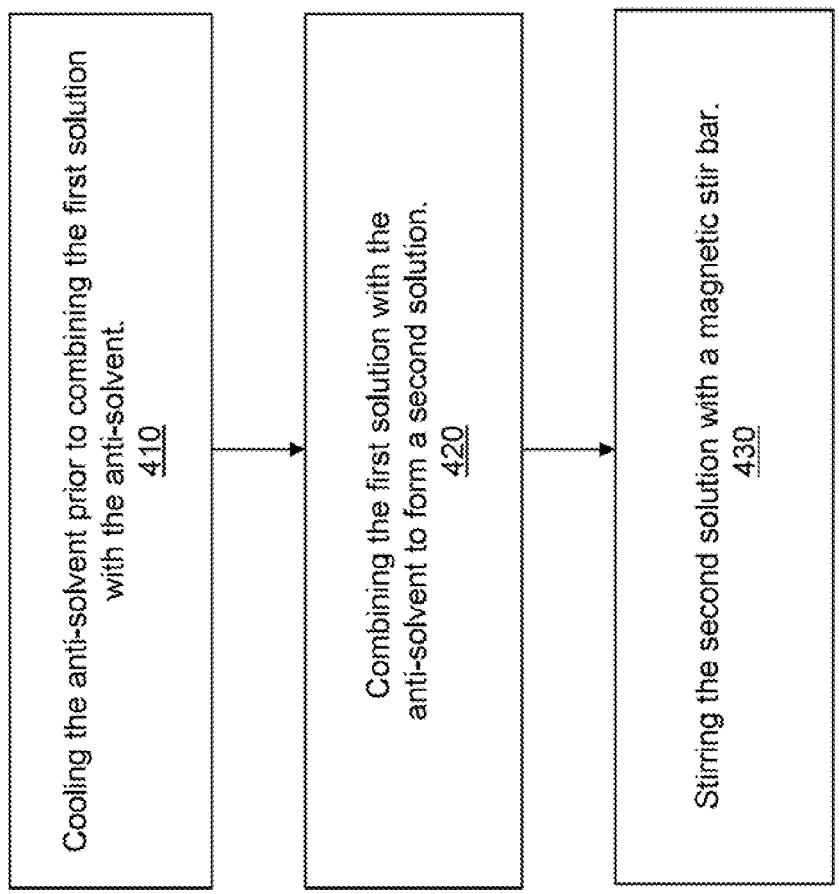
FIG. 4 is a flow chart showing a method of forming a second solution, according to an illustrative embodiment of the invention.

FIG. 4 is a flow chart showing a method 400 of forming a second solution, according to an illustrative embodiment of the invention.

The method involves cooling the anti-solvent prior to combining the first solution with the anti-solvent (Step 410). In various embodiments, cooling the anti-solvent involves freezing, refrigerating, maintaining at room temperature, or any combination thereof.

The method also involves combining the first solution with the anti-solvent to form a second solution (Step 420). In some embodiments, forming the second solution involves combining an amount of anti-solvent greater than an amount of solvent.

The method also involves stirring the second solution with a magnetic bar (Step 430). In various embodiments, stirring the second solution (e.g., performed by a human) and/or mechanical (e.g., performed by a machine).

Figure 5:
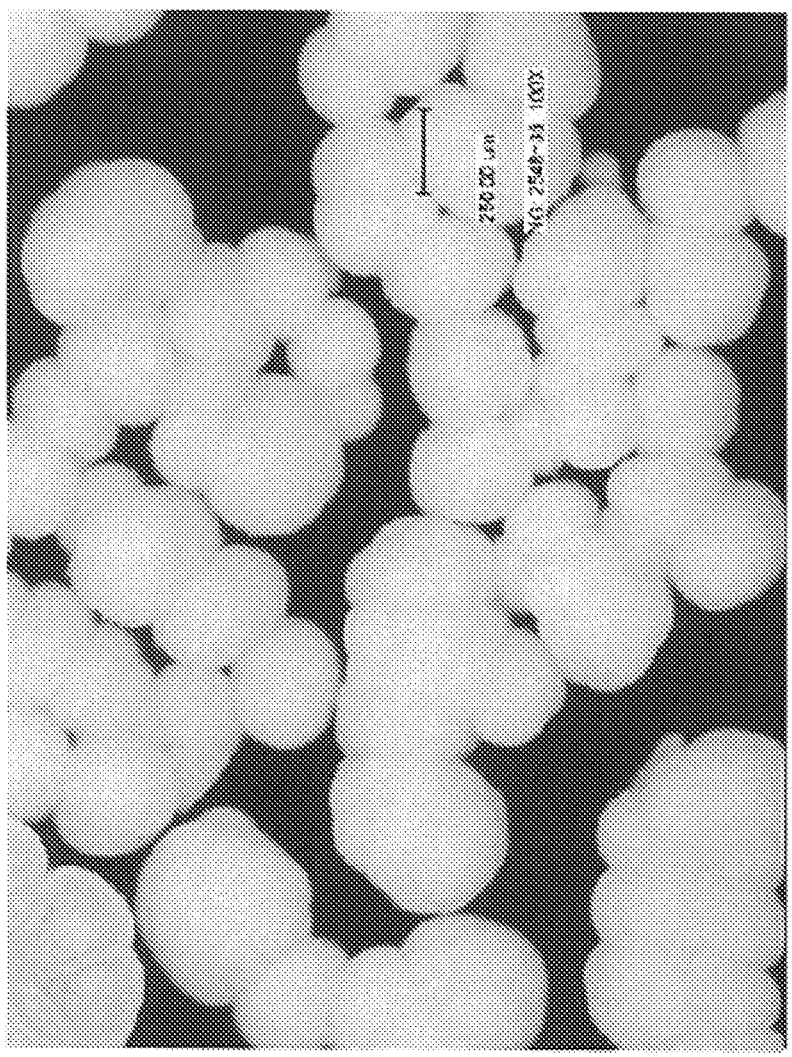
FIG. 5 is an exemplary image of spherical crystal habit NQ, according to illustrative embodiments of the invention.

Turning back to FIG. 1, the method also involves cooling the second solution (Step 140). In various embodiments, cooling the second solution involves freezing, refrigerating, maintaining at room temperature, or any combination thereof. In some embodiments, cooling the second solution is done by any mechanism that can cool the second solution without adding additional matter to the second solution. Cooling the second solution can cause crystals to precipitate. The crystals are substantially spherical shaped. In some embodiments, the crystals are spherical shaped with dimples and/or protrusions. In some embodiments, the crystals are spherical shaped NQ (e.g., as shown in FIG. 5).

Table 1 shows exemplary comparisons between high bulk density cubic NQ and spherical NQ for various safety tests, according to illustrative embodiments of the invention.

TABLE 1

| Test | NQ HBD | NQ Spherical |
|---|---|---|
| ABL Impact (cm, TIL[1]) | 64 | 80 |
| ABL Friction (ibs @ ft/s, TIL[1]) | 750 @ 8 | 750 @ 8 |
| ABL esd (Joules, TIL[1]) | 3.054 | 5.656 |
| SBAT[2] (Onset, ° F.) | 307 | — |

[1]Threshold Initiation Limit (20/20 NO GO tests)
[2]Simulated Bulk Autoignition Temperature (24° F./hr)

As shown in Table 1, the spherical NQ can have better electrostatic discharge and/or impact insensitivity then high bulk density cubic NQ.

Tables 2a and 2b show exemplary weights, volumes, and densities for multiple samples from two batches of spherical NQ, according to illustrative embodiments of the invention.

TABLE 2a

| Sample wt (g) | Volume (cc) | Density (g/cc) |
|---|---|---|
| 4.1790 | 2.4175 | 1.7286 |
| 4.1790 | 2.4133 | 1.7317 |
| 4.1790 | 2.4136 | 1.7314 |

TABLE 2b

| Sample wt (g) | Volume (cc) | Density (g/cc) |
|---|---|---|
| 3.6102 | 2.0162 | 1.7906 |
| 3.6102 | 2.0120 | 1.7943 |
| 3.6102 | 2.0151 | 1.7916 |

The average density of spherical NQ in the first batch shown in Table 2a is 1.7306 g/cc, with standard deviation of 0.0017 g/cc and range of 0.0030 g/cc. The average density of spherical NQ in the second batch shown in Table 2b is 1.7922 g/cc, with standard deviation of 0.0019 g/cc and range of 0.0037 g/cc. Table 3 shows exemplary vacuum thermal stability data for multiple samples from two batches of spherical NQ, according to illustrative embodiments of the invention.

TABLE 3

| | Batch 1 | | Batch 2 | |
|---|---|---|---|---|
| Sample | #1 | #2 | #1 | #2 |
| Wt. of Sample (g) | 1.0274 | 1.0531 | 1.0040 | 1.0028 |
| Density (Sample) (g/cc): | 1.700 | 1.700 | 1.700 | 1.700 |
| Temp$_{(i)}$ (deg C.): | 23.7 | 23.7 | 23.7 | 23.7 |
| Temp$_{(1)}$ (deg C.): | 24.3 | 24.3 | 24.3 | 24.3 |
| P$_{(i)}$ (psia): | 0.67 | 0.57 | 0.68 | 0.68 |
| P$_{(First Stab)}$ (psia): | 1.31 | 1.23 | 1.32 | 1.28 |
| P$_{(iSecond Stab)}$ (psia): | 1.58 | 1.51 | 1.60 | 1.55 |
| P$_{(f)}$ (psia): | 1.04 | 0.95 | 1.04 | 1.01 |
| Empty Tube Volume (ml): | 14.100 | 14.100 | 14.100 | 14.100 |
| Free Volume (ml): | 13.496 | 13.481 | 13.509 | 13.510 |
| Gas Volume (ml): | 0.311 | 0.319 | 0.303 | 0.277 |
| Gas Evolution (ml/g): | 0.303 | 0.303 | 0.302 | 0.277 |
| Average Gas Evolution (ml/g): | 0.303 | | 0.289 | |

The vacuum stability data in Table 3 is for samples having an approximate temperature of 100° C. over a 48 hour period, the sample within a tube volume of 14.100 mL. For example, Sample #1 of Batch 1 has a weight of 1.0274 g and density of 1.700 g/cc. Sample 1 also has a pressure in pounds per square inch absolute (psia) relative to vacuum of 0.67 psia, 1.31 psia, 1.58 psia, and 1.04 psia for P$_{(i)}$, P$_{(First Stab)}$, P$_{(iSecond Stab)}$, and P$_{(f)}$ respectively. The free volume of the Sample #1 is 13.496 ml, and a gas volume or Sample #1 is 0.303 ml/g.

As shown in Table 3, the average gas evolution of spherical NQ in the first batch is 0.303 mL/g. The average gas evolution of spherical NQ in the second batch is 0.289 mL/g.

Figure 6:
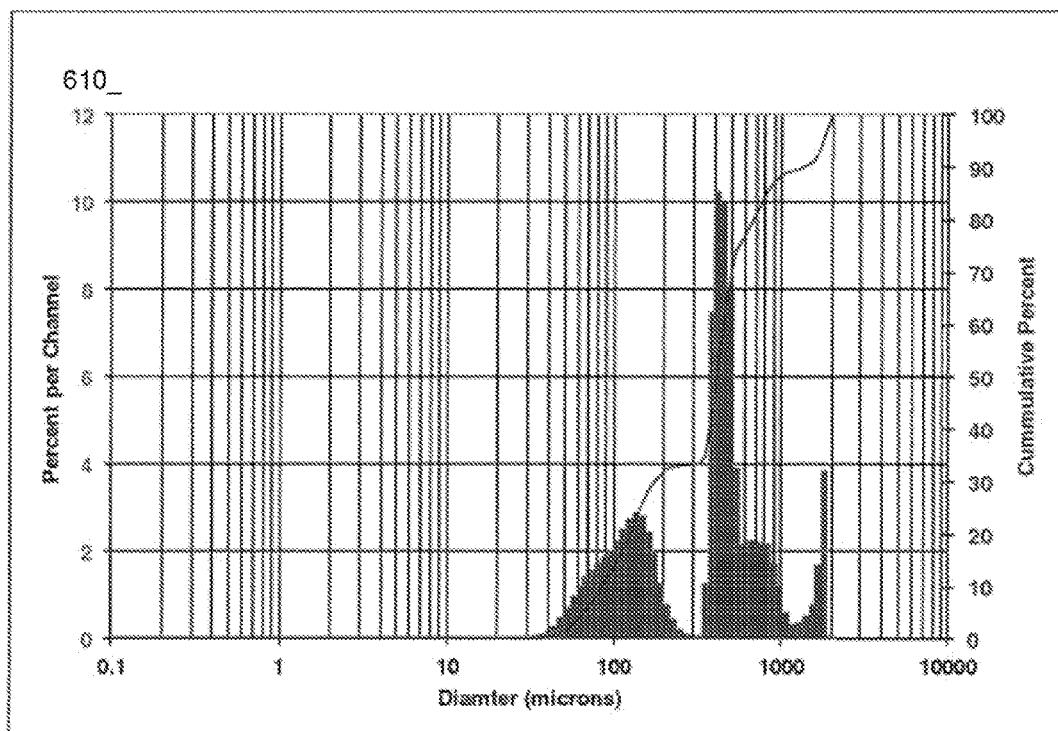
FIG. 6 are graphs showing particle size distribution for two batches of recrystallized spherical NQ, according to illustrative embodiments of the invention.
Figure 6:
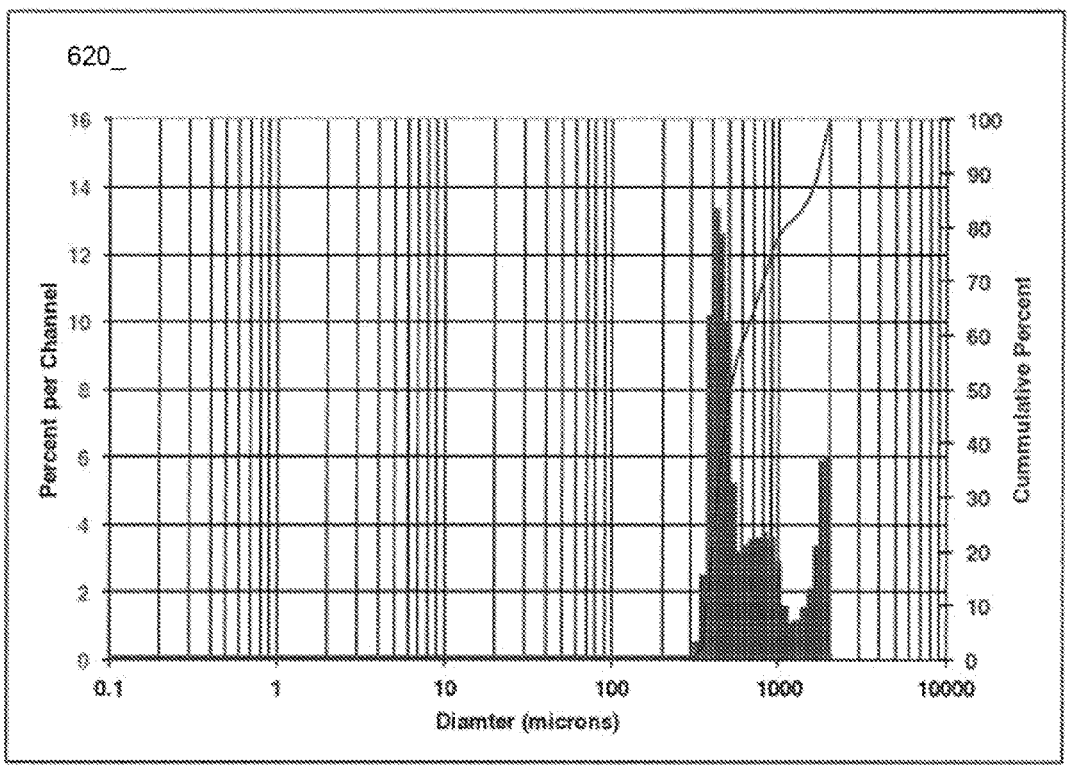
Figure 7:
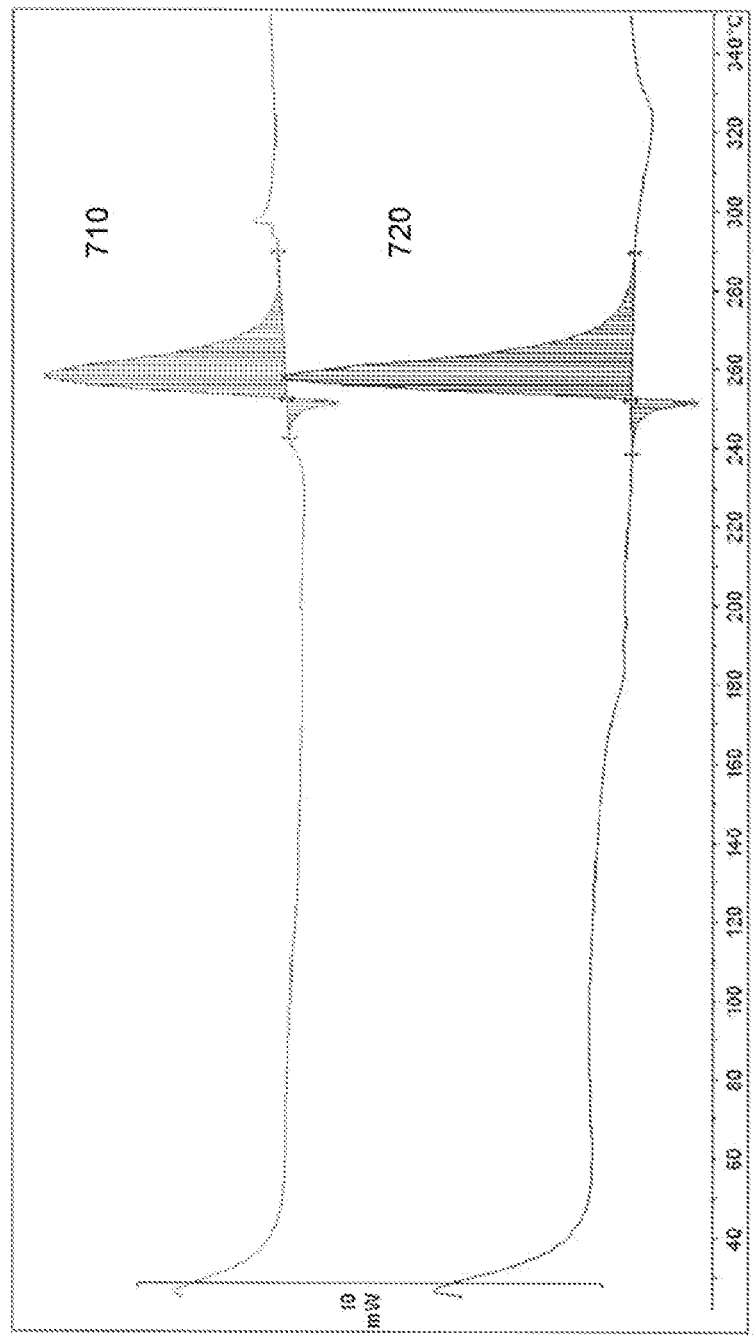
FIG. 7 are graphs showing differential scanning calorimetry of two samples of recrystallized spherical NQ, according to illustrative embodiments of the invention.

FIG. 6 are graphs 610 and 620, showing particle size distribution for two batches of recrystallized spherical NQ, according to illustrative embodiments of the invention. Graph 610 shows a cumulative percentage of particle diameter size distribution yielded 272.8 microns at 10%, 437.1 microns at 50%, and 844.3 microns at 90% for the first batch of recrystalized spherical NQ. Graph 620 shows a cumulative percentage of particle diameter size distribution yielded 377.4 microns at 10%, 638.9 microns at 50%, and 1361 microns at 90% for the second batch of recrystallized spherical NQ. FIG. 7 are graphs 710 and 720 showing differential scanning calorimetry of two samples of recrystallized spherical NQ, according to illustrative embodiments of the invention. The first batch has samples of 0.2070 mg and 0.2760 mg, respectively, of recrystallized spherical NQ. For the 0.2070 mg sample, the onset melting temperature is 247.78° C. and the peak melting temperature is 251.26° C. For the 0.2760 mg sample, the onset melting temperature is 247.91° C. and the peak melting temperature is 251.25° C.

Figure 8:
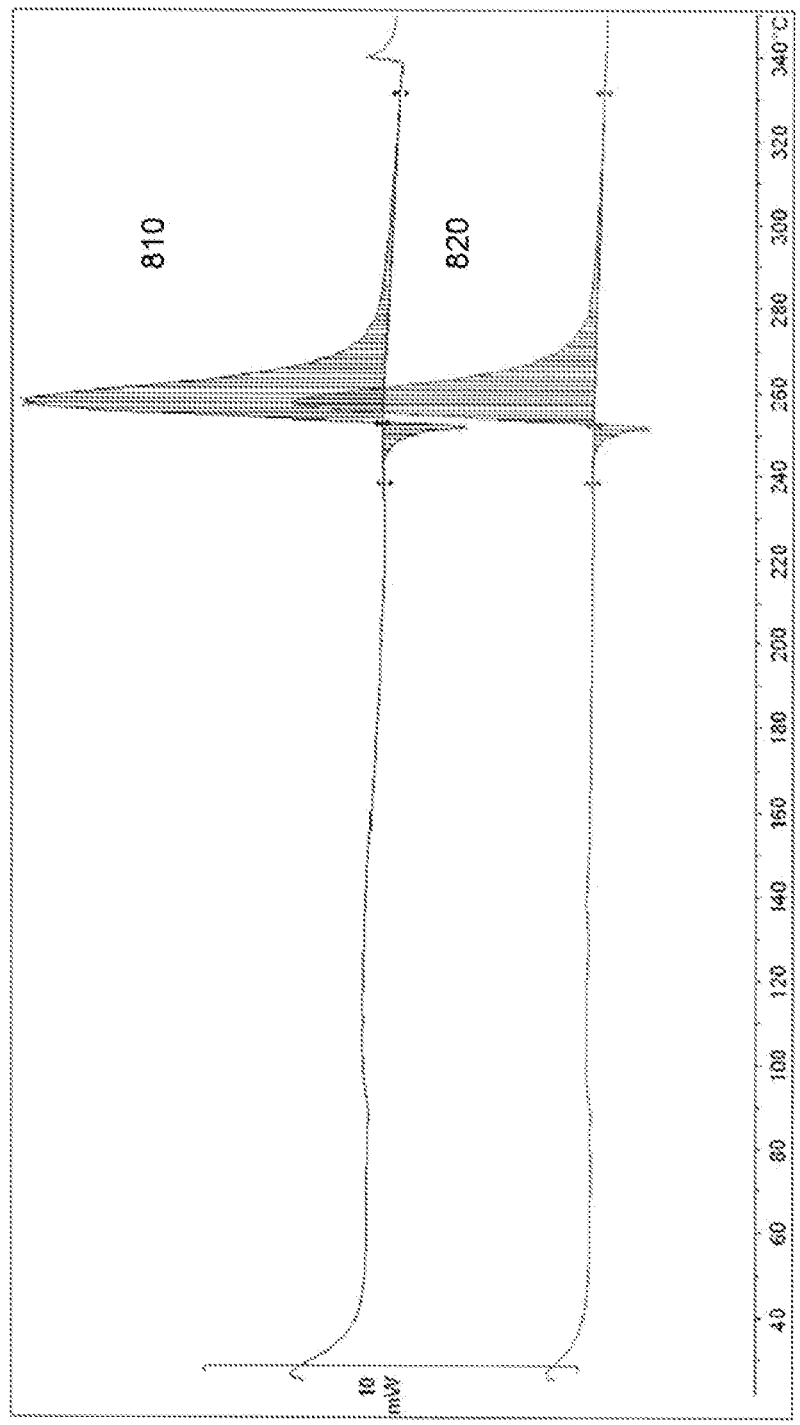
FIG. 8 are graphs showing differential scanning calorimetry of two samples of recrystallized spherical NQ, according to illustrative embodiments of the invention.

FIG. 8 are graphs 810 and 820 showing differential scanning calorimetry of two samples of recrystallized spherical NQ, according to illustrative embodiments of the invention. The second batch has samples of 0.3820 mg and 0.2360 mg, respectively, of recrystallized spherical NQ. For the 0.3820 mg sample, the onset melting temperature is 248.22° C. and the peak melting temperature is 251.56° C. For the 0.2360 mg sample, the onset melting temperature is 248.54° C. and the peak melting temperature is 251.28° C.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method of forming a spherical crystal habit, the method comprising:
   forming a first solution by combining a water-containing needle-shaped crystal habit, a solvent, and a surfactant;
   dissolving the water-containing needle-shaped crystal habit by heating the first solution to a predetermined temperature;
   forming a second solution by combining the first solution with an anti-solvent; and
   forming a high bulk density spherical crystal habit by cooling the second solution.

2. The method of claim 1 wherein the water-containing needle-shaped crystal habit is nitroguanidine.

3. The method of claim 1 wherein the water-containing needle-shaped crystal habit that is combined to form the first solution is 3 grams of nitroguanidine.

4. The method of claim 1 wherein the solvent comprises N-methylpyrrolidone.

5. The method of claim 1 wherein the solvent that is combined to form the first solution is 9 to 12 milliliters of N-methylpyrrolidone.

6. The method of claim 1 wherein the surfactant comprises Polysorbate 20.

7. The method of claim 1 wherein the surfactant that is combined to form the first solution is 50 to 150 microliters of Polysorbate 20.

8. The method of claim 1 wherein combining the needle-shaped crystal habit, the solvent, and the surfactant further comprises agitating the first solution.

9. The method of claim 8 wherein agitating the first solution further comprises shaking, stirring, manual combining, mechanical combining, or any combination thereof.

10. The method of claim 1 wherein combining the needle-shaped crystal habit, the solvent, and the surfactant further comprises stirring with a magnet.

11. The method of claim 1 wherein heating the first solution further comprises uniformly distributing heat to the first solution.

12. The method of claim 1 wherein the predetermined temperature is at least 80° C.

13. The method of claim 1 wherein dissolving the water-containing needle-shaped crystal habit further comprises shaking, stirring, manual combining, mechanical combining, or any combination thereof.

14. The method of claim 1 wherein dissolving the water-containing needle-shaped crystal habit further comprises stirring the first solution with a magnet.

15. The method of claim 1 wherein the anti-solvent comprises acetone.

16. The method of claim 1 wherein the anti-solvent is 120 to 200 milliliters of acetone.

17. The method of claim 1 wherein forming the second solution further comprises cooling the anti-solvent prior to combining the first solution with the anti-solvent.

18. The method of claim 17 wherein cooling the anti-solvent further comprises freezing, refrigerating, maintaining at room temperature, or any combination thereof.

19. The method of claim 1 wherein forming the second solution further comprises combining an amount of anti-solvent greater than an amount of solvent.

20. The method of claim 1 wherein forming the second solution further comprises shaking, stirring, manual combining, mechanical combining or any combination thereof 21. The method of claim 1 wherein forming the second solution further comprises stirring with a magnet.

22. The method of claim 1 wherein cooling the second solution further comprises freezing, refrigerating, maintaining at room temperature, or any combination thereof.

23. A method of forming a spherical crystal habit, the method comprising:
   forming a first solution by combining a water-containing needle-shaped crystal habit, a solvent, and a surfactant;
   agitating the first solution by shaking, stirring, manually combining, mechanically combining, or any combination thereof;
   dissolving the water-containing needle-shaped crystal habit by uniformly distributing heat to the first solution at a predetermined temperature of at least 80° C.;
   cooling an anti-solvent by freezing, refrigerating, maintaining at room temperature, or any combination thereof;
   forming a second solution by combining the first solution with the anti-solvent;
   agitating the second solution by shaking, stirring, manually combining, mechanically combining, or any combination thereof; and
   forming a high bulk density spherical crystal habit by cooling the second solution via freezing, refrigerating, maintaining at room temperature, or any combination thereof.

24. The method of claim 1 wherein the first solution is formed in a vessel having an inner surface area, the inner surface area of the vessel sized relative to an amount of the water-containing needle-shaped crystal habit combined to form the first solution.

* * * * *